United States Patent [19]

Atkins

[11] 4,380,634
[45] Apr. 19, 1983

[54] METHOD OF PREPARING 2-KETO-4,6,8,8-TETRAMETHYL-8,9-DIHYDRO-2H-PYRANO-(3,2-G) QUINOLINE, A BLUE-GREEN LASER DYE

[75] Inventor: Ronald L. Atkins, Ridgecrest, Calif.

[73] Assignee: The United States of America as represented by the Secretary of the Navy, Washington, D.C.

[21] Appl. No.: 308,014

[22] Filed: Oct. 5, 1981

Related U.S. Application Data

[63] Continuation-in-part of Ser. No. 951,907, Oct. 16, 1978, abandoned.

[51] Int. Cl.³ .......................................... C07D 471/04
[52] U.S. Cl. ................. 546/89; 252/301.17; 252/301.26; 8/444; 372/53; 372/54
[58] Field of Search .......................................... 546/89

[56] References Cited

U.S. PATENT DOCUMENTS

| | | | |
|---|---|---|---|
| 3,707,447 | 12/1972 | Alexander et al. | 204/49 |
| 3,857,793 | 12/1974 | Pappalardo et al. | 252/301.3 R |
| 3,860,886 | 1/1975 | McColgin et al. | 331/94.5 L |
| 3,986,140 | 10/1976 | Angadiyavar et al. | 331/94.5 L |
| 4,026,898 | 5/1977 | Henry et al. | 544/197 |
| 4,138,401 | 2/1979 | Hammond et al. | 546/89 |

OTHER PUBLICATIONS

Atkins et al., J. Org. Chem., 43, pp. 1975–1980 (1978).
Elderfield (Ed.), "Heterocyclic Compounds, vol. 4, (1952) pp. 22, 23 and 277.
Henry et al., J. Heterocylic Chem., vol. 14, pp. 1109–1114 (1977).
Hammond et al., Appl. Phys. 9 p. 67 (1976).
Woods et al., J. of Chem. & Eng. Data, vol. 13, No. 3, pp. 440–442 (1968).
Pechman, Berichte, 32, pp. 3681–3690 (1899).
Pechman et al., Berichte, 32, pp. 3696–3704 (1899).

*Primary Examiner*—Donald G. Daus
*Assistant Examiner*—D. B. Springer
*Attorney, Agent, or Firm*—R. F. Beers; W. T. Skeer; Bruce H. Cottrell

[57] ABSTRACT

A laser dye, 2-keto-4,6,8,8-tetramethyl-8,9-dihydro-2H-pyrano(3,2-g) quinoline, is prepared by mixing m-aminophenol and ethyl acetoacetate and heating the mixture.

2 Claims, No Drawings

METHOD OF PREPARING 2-KETO-4,6,8,8-TETRAMETHYL-8,9-DIHYDRO-2H-PYRANO-(3,2-G) QUINOLINE, A BLUE-GREEN LASER DYE

This application is a Continuation-In-Part of application Ser. No. 951,907 filed Oct. 16, 1978, now abandoned.

BACKGROUND OF THE INVENTION

This invention relates to laser dyes and more particularly, to a method of preparing a blue-green dye exhibiting a lasing action in the 455–480 nm range.

Organic dye molecules which will lase under flash lamp excitation do not possess both the necessary qualities of (i) high photostability and (ii) emission of laser light at the desired wavelength.

It would be desirable to provide a laser dye which emits light at the desired wavelength of 455–480 nanometers (nm), has enhanced photostability, and is tunable over the lasing range.

OBJECTS OF THE INVENTION

It is, therefore, an object of this invention to provide a novel laser dye. A further object of this invention is to provide a method for preparing such a laser dye.

These and still further objects, features and advantages of the present invention will become apparent upon consideration of the following detailed disclosure.

BRIEF SUMMARY OF THE INVENTION

These and still further objects of the present invention are achieved, in accordance therewith, by providing a method of preparing a dye 2-Keto-4,6,8,8-tetramethyl-8,9-dihydro-2H-pyrano(3,2-g) quinoline. The dye is prepared by mixing m-aminophenol and ethyl acetoacetate in the molar ratio of approximately 1:2 in the absence of a catalyst, a condensing agent, or solvent and heating the mixture to 150° C. for six hours and then filtering out the dye.

DESCRIPTION OF THE PREFERRED EMBODIMENT

The following example describes the preparation of the dye.

EXAMPLE

2-Keto-4,6,8,8-tetramethyl-8,9-dihydro-2H-pyrano(3,2-g)-quinoline.

m-Aminophenol (10 g; 92 mmol) and ethyl acetoacetate (20 ml; 158 mmol) were mixed (approximate molar ratio of m-Aminophenol to ethyl acetoacetate is 1:2).

Upon heating the mixture to 150° C., a clear solution was obtained. As heating continued a yellow precipitate formed. Heating was continued for a total of six hours. The precipitate was filtered from the hot solution and washed with cyclohexane. A further 2.2 g of yellow solid was obtained from the cooled filtrate. Crystallization from methanol gave beautiful golden needles (mp 270°–274° C.): NMR (Me$_2$SO-d$_6$) $\delta$1.68 (s, 6,8-gem-dimethyls), 2.29 (d, 3, J=2 Hz, 6-Me), 2.72 (d, 3, J=1.6 Hz, 4-Me), 5.8 (bs, 1, H-7), 6.25 (q, 1, J=1.6 Hz, H-3), 6.71 (s, 1, H-10), 7.1 (bs, 1, NH), 7.48 (s, 1, H-5): IR 3311 (NH), 1695 cm$^{-1}$ (C=O); MS m/e 255, M+. Anal. Calcd: C, 75.27; H, 6.71; N, 5.49. Found: C, 75,67; H, 6.87; N, 5.45.

To use the dye in a laser, one forms a solution of it in a suitable solvent such as ethanol, places the solution in a nitrogen or flash lamp laser and pumps. A solution that is about 10$^{-3}$ molar in the dye is preferred. The dye solution could also be made with other polar solvents such as water and methanol.

The dye of this invention fluoresces strongly at 470 nm with high stability and exhibits lasing action over a 25 nm range (455–480 nm).

Obviously many modifications and variations of the present invention are possible in light of the above teachings. It is therefore to be understood that within the scope of the appended claims the invention may be practiced otherwise than as specifically described.

What is claimed is:

1. A method for preparing 2-keto-4,6,8,8-tetramethyl-8,9-dihydro-2H-pyrano(3,2-g) quinoline consisting of:
   mixing m-aminophenol and ethyl acetoacetate in the molar ratio of approximately 1:2 to form a mixture in the absence of a catalyst, or solvent;
   heating said mixture at 150° C.; and
   filtering 2-keto-4,6,8,8-tetramethyl-8,9-dihydro-2H-pyrano(3,2-g) quinoline.

2. A method according to claim 1 wherein said heating is carried out for six hours.